United States Patent [19]

Hahn et al.

[11] Patent Number: 5,455,229
[45] Date of Patent: Oct. 3, 1995

[54] METHOD FOR MINIMIZING AND CONTAINING ISCHEMIC AND REPERFUSION INJURY

[75] Inventors: Richard A. Hahn, Carmel; Brian R. MacDonald, Fairland; Robert T. Shuman, Greenwood; Gerald F. Smith, Indianapolis, all of Ind.

[73] Assignee: Eli Lilly and Company, Indianapolis, Ind.

[21] Appl. No.: 996,347

[22] Filed: Dec. 23, 1992

[51] Int. Cl.$^6$ .................................................. A61K 38/06
[52] U.S. Cl. .............................. 514/18; 514/19; 530/331; 562/560; 562/445; 548/535
[58] Field of Search ...................... 514/18, 19; 530/331; 562/560, 445; 548/535

[56] References Cited

U.S. PATENT DOCUMENTS 4,703,036  10/1987  Bajusz et al. .

FOREIGN PATENT DOCUMENTS

0479489A2  9/1991  European Pat. Off. .

OTHER PUBLICATIONS

Jackson, J Pharmacol Exp Ther 261, 546, 1992.
Eisenbach, et al., *Pharmacological Research Communications*, 9: 1, pp. 79–92 (1977).
Shimai, et al., *Japanese Circulation Journal*, 53, pp. 1144–1151 (1989).
Thiemermann, et al., *Br. J. Pharmacol.* 97, pp. 401–408 (1989).
Bajusz, et al., *J. Med. Chem*, 33, pp. 1729–1735 (1990).
Geeraerts *Am J Physiol* 261, C889 1991.
Bolli *J Am Cell Cardiol* 2, 681, 1983.

*Primary Examiner*—Jill Warden
*Assistant Examiner*—David Lukton
*Attorney, Agent, or Firm*—Ronald S. Maciak; David E. Boone; Gerald V. Dahling

[57] ABSTRACT

The present invention is a method for minimizing and containing injury caused when tissue is subject to ischemia and reperfusion. The method comprises administering certain derivatized tripeptide arginal compounds concurrent with, or immediately after, reestablishing blood flow to the ischemic tissue. The method is particularly useful for minimizing and containing damage to the heart during evolving myocardial infarction.

22 Claims, No Drawings

METHOD FOR MINIMIZING AND CONTAINING ISCHEMIC AND REPERFUSION INJURY

TECHNICAL FIELD

This invention relates to the discovery that a group of known tripeptide arginal derivatives are useful for minimizing and containing damage caused when tissue is subject to ischemia and reperfusion. The method is particularly useful as a cardioprotectant for containing ischemic damage caused during evolving myocardial infarction and reperfusion.

BACKGROUND

Ischemia occurs when blood flow to an area of cells is insufficient to support normal metabolic activity. If the condition persists for an extended period, the cells within the ischemic zone die. Reperfusion is the term used to describe the act of reestablishing blood flow to ischemic tissue. Hence, reperfusion is essential to the future survival of cells within an ischemic area. However, it is well known that reperfusion itself causes irreparable damage to many cells that survived the ischemic event. Therefore, compounds capable of minimizing and containing ischemic or reperfusion damage represent important therapeutic agents.

Reperfusion damage is largely the result of inflammatory processes. Reperfused ischemic tissue attracts leukocytes which release proteolytic enzymes and oxidants that in turn promote further inflammation followed by eventual healing and scarring. Since leukocyte-derived proteolytic enzymes and oxidants are non-selective, they degrade normal and reversibly injured tissue. Therefore, dampening the inflammatory response or inhibiting the most harmful agents in the inflammatory process are logical approaches for minimizing and containing reperfusion injury.

Evolving myocardial infarction is an ongoing process where the myocardium fails to receive adequate blood supply to support normal metabolic activity and is typically caused by coronary artery occlusion. Because of the constant, relatively high metabolic activity of the heart and the many therapies for alleviating coronary artery occlusion, evolving myocardial infarction is probably the most common, and serious setting for reperfusion injury.

Numerous therapeutic interventions, such as angioplasty, bypass surgery, and thrombolytic regimens, recannalize occluded coronary arteries and lead to myocardial reperfusion injury. See Lucchesi et al.; Leukocytes and Ischemia-induced Myocardial Injury, *Ann. Rev. Pharmacol. Toxicol.* 36: 159–163 (1985); and Engler, R. L.; Free Radical and Granulocyte-Mediated Injury during Myocardial Ischemia and Reperfusion, *Am. J. Cardiol.* 63: 19E–23E (1989).

Because recruited leukocytes have been implicated in extending myocardial infarction caused by coronary artery occlusion and reperfusion, neutrophil intervention is a logical approach for minimizing and containing evolving myocardial infarction. Such neutrophil interventions include neutropenia induction, anti-adhesion molecule monoclonal antibodies, and oxidant scavengers. See Romson et al.; Reduction of the Extent of Ischemic Myocardial Injury by Neutrophil Depletion in the Dog, *Circulation* 67: 1016–1023 (1983); Mullane et al.; Role of Leukocytes in Acute Myocardial Infarction in Anesthetized Dogs: Relationship to Myocardial Salvage by Antiinflammatory Drug, *J. Pharmacol. Exp. Ther.* 228: 510–522 (1984); Mitsos et al.; Protective Effects of N-2-Mercaptopropionyl Glycine against Myocardial Reperfusion Injury after Neutrophil Depletion in the Dog: Evidence for the Role of Intracellular-derived Free Radicals, *Circulation* 73: 1077–1086 (1986); Mitsos et al.; Canine Myocardial Reperfusion Injury: Protection by a Free Radical Scavenger, N-2-Mercaptopropionyl Glycine, *J. Cardiovasc. Pharmacol.* 8: 978–988 (1986); Jolly et al.; Canine Myocardial Reperfusion Injury: Its Reduction by the Combined Administration of Superoxide Dismutase and Catalase. *Circ. Res.* 54: 277–285 (1984); Simpson et al.; Reduction of Experimental Canine Myocardial Ischemia and Reperfusion Injury by a Monoclonal Antibody (Anti-Mol) that Inhibits Leukocyte Adhesion. *Circulation* 76: A0799, (1987); and Jolly et al.; Reduction of Myocardial Infarct Size by Neutrophil Depletion: Effect of Duration of Occlusion. *Am. Heart J.* 112: 682–690 (1986).

It has now been unexpectedly found that a group of compounds known to inhibit the action of several proteases are capable of containing and minimizing tissue damage caused by ischemia and reperfusion. The compounds are especially useful in a novel method for minimizing the detrimental effects to the heart caused during myocardial infarction and reperfusion.

SUMMARY OF THE INVENTION

The invention is a method for minimizing and containing reperfusion injury comprising administering, to an mammal in need of such treatment an effective non-toxic amount of a compound of the general formula:

A-Pro-Arg-H wherein the chiral center for A is DL, preferably D, L for Pro, and L for Arg;

A is

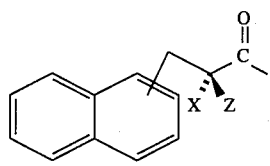

,

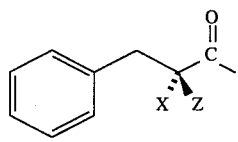

, 1 or 2

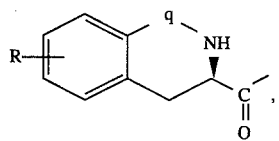

,

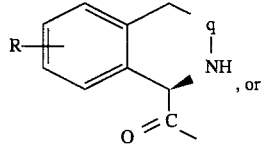

, or

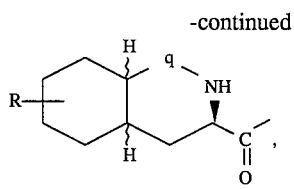

Z is $C_1$–$C_4$ alkyl, or H;

X is $NH_2$, NHZ, t-butyloxycarbonyl-NH, acetyl-NH, or trifluoroacetyl-NH;

R is H, OH, halogen, alkoxy, $CF_3$, $C_1$–$C_4$ alkyl, $NO_2$, or $NH_2$; and, q is $CH_2$, or CO.

DETAILED DESCRIPTION OF THE INVENTION

Compounds useful in the method of the present invention are generally known in the art. See U.S. Pat. No. 4,703,036, herein incorporated by reference and European Patent Application Publication EP-A-0 479 489, and Bajusz et al.; Highly Active and Selective Anticoagulants: D-Phe-Pro-Arg-H, a Free Tripeptide Aldehyde Prone to Spontaneous Inactivation, and Its Stable N-Methyl Derivative, D-MePhe-Pro-Arg-H, *J. Med. Chem.* 33: 1729–1735 (1990). The compounds are tripeptide arginal derivatives having the general formula A-Proline-Arginine-aldehyde+tm (formula 1)

The A substituent of formula 1 is defined by the following structures:

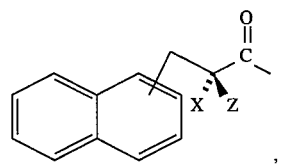

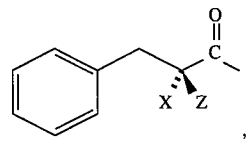

1 or 2

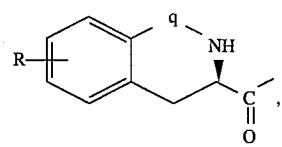

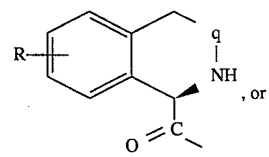
, or

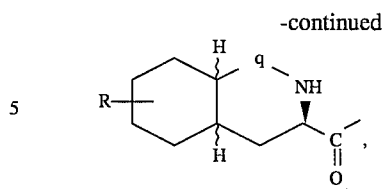

wherein Z is $C_1$–$C_4$ alkyl, or H; X is $NH_2$, NHZ, t-butyloxycarbonyl-NH, acetyl-NH, or trifluoroacetyl-NH; R is H, OH, halogen, alkoxy, $CF_3$, $C_1$–$C_4$ alkyl, $NO_2$, or $NH_2$; and, q is $CH_2$, or CO.

The α-carbons of the proline and arginine residues are in the L configuration, and the α-carbon of the A substituent is DL, preferably D.

Pharmaceutically acceptable salts of the compounds of formula 1 are also useful in the instant method and include the acid addition salts formed with inorganic acids and carboxylic acids. Examples of inorganic acids forming salts are the hydrohalic acids, particularly hydrochloric and hydrobromic, phosphoric acid and sulfuric acid. Carboxylic acid salts are formed with acids such as acetic, propionic, malonic, maleic, citric, succinic, malic, benzoic, fumaric, and like carboxylic acids. The acid addition salts are prepared in a conventional manner e.g. by neutralizing the free base form of the compound 1 with the acid. Preferred acid addition salts are sulfate and hydrochloride salts.

The compounds represented by the formula 1 are prepared by well known methods of peptide coupling. See generally Dugas and Penney, *Bioorganic Chemistry* 13–82 (1981). According to one such method the acid ACOOH, wherein A has the same meanings as defined for formula 1, is coupled with a carboxy protected proline to form the dipeptide (when A is an amino acid) or an N-acylproline ester (when A is other than an amino acid). The carboxy protecting ester group of the proline moiety of the product is removed and the free acid form of the dipeptide is coupled with the lactam form of arginine. The above reaction sequence is illustrated by the following scheme.

ACOOH + proline ester ⟶

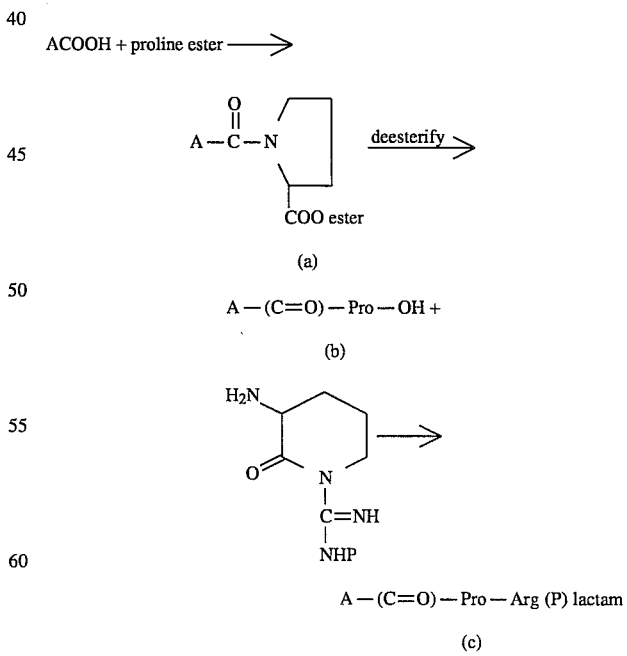

wherein P represents an amino protecting group.

The coupled Arg(P) lactam product (c) is reduced with lithium aluminum hydride in an inert solvent to cleave the lactam ring and provide the tripeptide in the arginine aldehyde form represented by the formula
A(C=O)-Pro-Arg(P)-H
wherein Arg(P)-H represents amino protected arginine aldehyde.

The lactam form of arginine is obtained by intramolecular coupling of amino protected arginine [Arg-OH]. For example, Boc-Arg(Cbz)OH represented by the formula

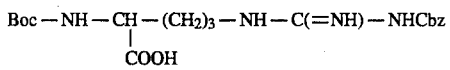

wherein Boc=t-butyloxycarbonyl and Cbz=benzyloxycarbonyl, is first converted to an active ester form, such as an active mixed anhydride, with a chloroformate ester, e.g. ethyl chloroformate to isobutyl chloroformate. The ester formation is carried out in the presence of a tertiary amine such as N-methylmorpholine. Addition of a stronger tertiary amine base such as triethylamine effects the internal acylation to provide the lactam form of the di-amino protected arginine as shown below.

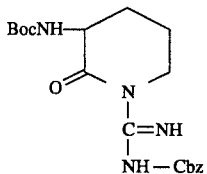

Prior to use in the coupling with the A(C=O)-Pro-OH as shown in the above scheme, the Boc protecting group is selectively removed with trifluoroacetic acid to provide the requisite free amino group.

The coupling of an ACOOH compound with a proline ester, when A is an amino acid residue, is carried out by first protecting the amino group of the amino acid. Conventional amino protecting groups commonly used for temporary protection or blocking of the amino group are employed. Examples of such protecting groups include the alkoxy, alkenyloxy, cycloalkoxy and aryloxycarbonyl groups such as ethoxycarbonyl, t-butyloxycarbonyl, cyclohexyloxycarbonyl, adamantyloxycarbonyl, trichloroethoxycarbonyl, benzyloxycarbonyl, diphenylmethoxycarbonyl, and like groups.

The ester group employed to protect the carboxy group of proline during the coupling reaction can be any of the commonly used readily removable ester groups such as t-butyl, benzyl, p-nitrobenzyl, p-methoxybenzyl, diphenylmethyl, trichloroethyl, phenacyl, or trialkylsilyl esters. In carrying out the coupling reaction one employs an ester group for proline which is removable by conditions under which the amino protecting group remains intact. The amino protecting group of the acylating acid A-COOH thus remains in place for protection of the amino group during the subsequent coupling with the arginine lactam compound to form A-(C=O)-Pro-Arg(P)lactam.

The coupling reactions described above are carried out in the cold preferably at a temperature between about −20° C. and about 15° C. The coupling reactions are carried out in an inert organic solvent such as dimethylformamide, dimethylacetamide, tetrahydrofuran, methylene chloride, chloroform, and like common solvents. Generally anhydrous conditions are used when, in the coupling reaction, an active ester of the acylating acid is used.

The compounds of the invention are preferably isolated in the form of acid addition salts. Salts of the compounds of formula 1 formed with acids, such as those mentioned hereinabove, are useful as pharmaceutically acceptable salts for administering the reperfusion injury-minimizing agents and for preparation of formulations of these agents. Other acid addition salts may be prepared and used in the isolation and purification of the peptides. For example, the salts formed with the sulfonic acids such as methanesulfonic acid, n-butanesulfonic acid, p-toluenesulfonic acid and naphthalene sulfonic acid may be so used.

Methods for isolating and purifying the compounds represented by the formula 1, while at the same time preparing a desired stable salt form, are known in the art. According to one such method, stable salts of inorganic acids, including the sulfate and hydrochloride salts, are provided by preparative purification over $C_{18}$ reversed-phase chromatography. The aqueous phase comprises sulfuric acid or hydrochloric acid at a concentration between about 0.01% and about 0.05% and acetonitrile, THF (tetrahydrofuran), methanol or other suitable solvents serve as the organic component. The pH of the acidic eluant is adjusted to between about pH 4 and about pH 6. The exact pH is a function of the particular peptide with a basic resin (e.g. Bio-Rad AG-1X8) in the hydroxyl form. After pH adjustment the solution of the tripeptide salt, e.g. sulfate or hydrochloride, is lyophilized to provide the purified salt dry powder form.

The most preferred compounds of formula 1 that are particularly useful in the present invention are:

Compound 1: D-3-Piq-L-Prolyl-L-Arginal (sulfate salt)

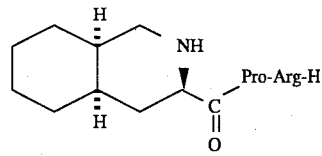

Compound 2: D-7-hydroxyl-1,2,3,4-Tiq-3-carbonyloxy-L-Prolyl-L-Arginal (dihydrochloride salt)

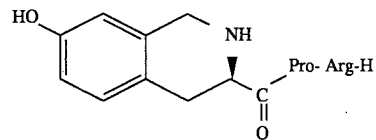

Compound 3: D-3-Tiq-L-Prolyl-L-Arginal (sulfate salt)

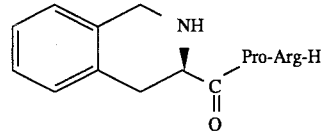

Compound 4: D-1,2,3,4-Tiq-1-carbonyl-L-Prolyl-L-Arginal (salt)

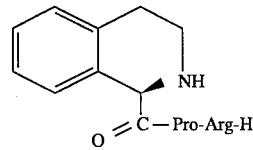

Compound 5: N-Methyl-D-Phenylalanyl-L-Prolyl-L-Arginal (salt)

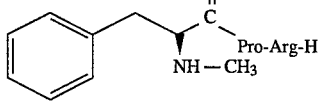

Compound 6: N^α-t-butyloxycarbonyl-D-Phenylanyl-L-Prolyl-L-Arginal (salt)

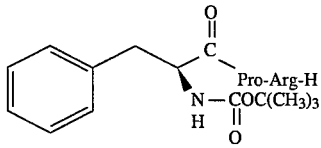

The present invention is practiced by administering a compound of formula 1 to a mammal so that an effective concentration of the compound is in the blood stream at about the time when adequate blood flow is reestablished to an ischemic zone of cells. Preferably, an effective amount of the compound will be in the blood stream when satisfactory blood flow to the ischemic area is reestablished. However, achieving an effective blood level of the compound just after the ischemic area is reperfused is also consistent with the instant method.

The compound may be administered orally, parenterally e.g. by intervenous infusion or injection or a combination of injection and infusion (iv), intramuscularly (im), or subcutaneously (sc). Preferably, administration is carried out by iv infusion. An effective blood level concentration of the compound should be maintained for at least an hour after reperfusion and up to several days depending on the relative potency of the compound and the size of the ischemic zone involved.

Effective doses range from about 5 mg to about 1000 mg, and the dose regimen will vary depending on the route of administration. Oral, im, and sc routes will require administrating the compound well before reestablishing blood flow to the ischemic tissue to allow the compound to enter the blood stream.

In the preferred embodiment, the infusion rate is in the range of about 0.2 to 5.0 mg/kg/hr for 1 to 10 hours. An infusion rate of about 0.5 to 2.0 mg/kg/hr for 1 to 10 hours is more highly preferred. In the case of a myocardial infarction caused by an occlusive thrombus, a compound of the invention may be co-administered with, or immediately following, thrombolytic treatment.

In another embodiment of the invention, a compound of formula 1 is co-administered with an oxidant scavenger. Illustrative examples of oxidant scavengers that are not meant to limit this aspect of the invention in any way include superoxide dismutase and N-mercaptopropionyl glycine. For purposes of this document, co-administration is meant to include administering a short time before or after the administration of a compound of formula 1. Co-administration also means that an effective amount of the co-administered compound is in the blood with an effective amount of a compound of formula 1.

In yet another embodiment of the invention, a compound of formula 1 is co-administered with a beta blocker. Illustrative examples of beta blockers that are not meant to limit this aspect of the invention in any way include Propranolol, Metoprolol, and Atenolol. And another embodiment of the invention includes co-administering a compound of formula 1 with aspirin. The invention further encompasses co-administering of a compound of formula 1 with some combination an oxidant scavenger, beta blocker, or aspirin.

The following examples are provided to help describe how the invention is practiced and to illustrate the intended benefits of the claimed methods. The example are not meant to limit the scope of the invention in any way.

The abbreviations used in the examples have the following meanings.
Amino acids: Arg=arginine, Pro=proline
Boc=t-butyloxycarbonyl
Bzl=benzyl
Cbz=benzyloxycarbonyl
DCC=dicyclohexylcarbodiimide
DMF=dimethylformamide
DMSO=dimethylsulfoxide
FAB-MS=fast atom bombardment mass spectrum
FD-MS=field desorption mass spectrum
THF=tetrahydrofuran
TLC=thin layer chromatography
Tiq=Tetrahydroisoquinoline
D-1-Tiq=D-1,2,3,4-Tetrahydroisoquinoline-1-carboxylic acid
D-3-Tiq=D-1,2,3,4-Tetrahydroisoquinoline-3-carboxylic acid
D-3-Piq=D-1,2,3,4,5,6,7,8-perhydroisoquinoline-3-carboxylic acid
L-Arg-H=L-arginal=

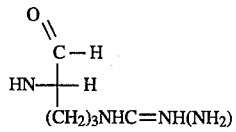

The $R_f$ values in the following examples were determined by silica gel thin layer chromotography (Kieselgel 60 F-254) in the following systems:
(A) Chloroform-Methanol-Acetic Acid 135:15:1
(B) Ethylacetate-Acetic Acid-Absolute Alcohol 90:10:10
(C) Chloroform-Methanol-Acetic Acid 90:30:5

EXAMPLE 1

Synthesis of D-1,2,3,4-tetrahydroisoquinoline-1-carbonyl-L-Prolyl-L-Arginal

DL-1,2,3,4-Tetrahyro-1-isoquinolinecarboxylic acid (1)

A solution of 1-isoquinolinecarboxylic acid (12.5 g, 0.072 mol) in glacial acetic acid (185 mL) was reacted with hydrogen over platinum oxide (2 g) at 60 psi in a Parr shaker apparatus at room temperature for 24 h. The reaction mixture was filtered through a Celite pad, and the filtrate was concentrated in vacuo. The solid was triturated with water, filtered, and dried to give pure title compound (8 g, 63%) FD-MS 178 (MH$^+$); $^1$HNMR (DMSO) d 2.80–3.00 (m, 3H), 3.10–3.20 (m, 1H), 3.30–3.40 (m, 2H), 7.05–7.25 (m, 4H), 7.65–7.75 (m, 1H).

t-Butyloxycarbonyl-DL-1,2,3,4-tetrahydro-1-isoquinolinecarboxylic acid DCHA (2)

A solution of 1,2,3,4-Tetrahyro-1-isoquinolinecarboxylic acid (1) (7.08 g, 0.040 mol) was dissolved in 2N NaOH (40 mL, 0.080 mol) and t-butyl alcohol (40 mL). Di-tert-butyl dicarbonate (10.5 g, 0.048 mol) was then added to the reaction mixture. After 24 h at room temperature the bulk of the t-butyl alcohol was evaporated, and the resulting aqueous solution was extracted once with diethyl ether. The aqueous layer was separated and acidified with 2N HCl to pH 2.0 and extracted with ethyl acetate. The organic solution was dried over magnesium sulfate and concentrated to dryness in vacuo. The resulting oil was dissolved in diethyl ether, followed by the addition of dicyclohexyl amine (7.9 mL, 0.040 mol) to the solution. After standing at 4° C. (4 h), the precipitate was filtered, washed with diethyl ether, and dried in vacuo to afford pure product (15.7 g, 86%) FD-MS 459 (MH$^+$); Anal. Calcd. for $C_{27}H_{42}N_2O_4$: C, 70.71; H, 9.23; N, 6.11. Found: C, 71.07; H, 9.37; N, 5.87.

Boc-D-1-Tiq-Pro-OH (3)

Boc-DL-1-Tiq-ODCHA (2) (73.4 g, 160 mmole) was suspended in EtOAc (200 ml), washed with 1.5N citric acid, then washed with water, and dried over magnesium sulfate. The EtOAc was concentrated to dryness in vacuo. The oil was dissolved in EtOAc, cooled to 0° C. and 2,4,5-trichlorophenol (31.6 g, 160 mmole) was added followed by DCC (33 g, 160 mmole). The reaction mixture was stirred for 1 hr at 0° C. then warmed to room temperature and stirred 1.5 hrs. The reaction mixture was cooled to 0° C., and the 5 hrs. The reaction mixture was cooled to 0° C., and the precipitate was filtered. The mother liquor was concentrated to dryness in vacuo. The resulting oil was dissolved in pyridine (100 ml). Proline 18.42g, 160 mmole), and triethylamine (22.3 ml, 160 mmole) was then added to the reaction mixture. After 24 hr at room temperature, the solvent was concentrated to dryness in vacuo. The resulting residue was dissolved in EtOAc/water and the pH adjusted to 9.5 with 2N NaOH. The aqueous layer was separated and acidified with 2N HCl to pH 2.0. The acidified aqueous layer was then extracted with ethyl acetate. The organic solution was dried over magnesium sulfate and concentrated to dryness in vacuo. The resulting oil was dissolved in methylene chloride and EtOAc. The solution was held at 4° C. for 4 hr, and the precipitate was filtered, washed with EtOAc, and recrystalized once from methylene chloride/EtOAc. The solid was dried in vacuo to afford pure product (19.6 g, 33%) TLC R$_f$ (A) 0.44; FAB-MS 375 (MH$^+$); Anal. Calcd. for $C_{20}H_{26}N_2O_5$: C, 64.15; H, 7.00; N, 7.48. Found: C, 63.26; H, 6.98; N, 7.52; [a]$_D$=+43.14° C=0.5 MeOH Boc-Arg(CBZ)-OH (4)

Boc-Arg(HCL)-OH (82.1 g, 250 mmole) was dissolved in 5N NaOH (240 ml) in a 3 necked R.B. flask. The reaction was chilled to −5° C., and the pH was maintained between 13.2 to 13.5 using 5N NaOH (250 ml) while dropwise adding benzylchloroformate (143 ml, 1.0 mole, 4 eq) over a 55 min period. The reaction was stirred for an additional 1 hr at −5° C. It was then diluted with 100 ml of water and 500 ml of Et$_2$O. The aqueous layer was separated and extracted twice with Et$_2$O (500 ml). The aqueous layer was with EtOAc (550 ml). The aqueous layer was separated and extracted once with EtOAc. The combined organic layers were washed with water then dried over magnesium sulfate. The organic layers were concentrated to dryness in vacuo to give 66.1 g of the title compound (65% of theory): TLC R$_f$ (C) 0.43; FD-MS 408 (M$^+$); $^1$HNMR (CDCl$_3$) d 1.42 (s, 9H), 1.61–1.91 (m, 4H), 3.23–3.41 (m, 2H), 4.17 (d, 1H), 5.21 (s, 2H), 5.62 (d, 1H), 7.30–7.42 (m, 6H), 8.37 (m, 1H).

Boc-Arg(Z)-Lactam (5)

Boc-Arg(Z)-OH (4) (66.0 g, 0.162 mole) was dissolved in dry THF (230 ml) and cooled to −10° C. in an ice-acetone bath. Triethylamine (23.5 ml, 1.05 eq), followed by isobutylchloroformate (22.5 ml, 1.05 eq) was then added to the solution. The reaction was stirred for 5 min at −10° C., followed by the addition of N-methylmorpholine (18.7 ml, 1.05 eq). The reaction was stirred for 1 hr at −10° C. then stirred for 1 hr at R.T. The reaction was poured into ice-water (1 L) and the resulting precipitate was filtered, washed with cold water, then dried in vacuo. The product was crystalized from EtOAc to give 38.05 g (60% of theory) of title compound: TLC R$_f$ (A) 0.77; FD-MS 391 (MH$^+$); $^1$HNMR (CDCl$_3$) d 1.48 (s, 9H), 1.78–1.98 (m, 2H), 2.50 (m, 1H), 3.41 (m, 1H), 4.43 (m, 1H), 4.90 (m, 1H), 5.16 (s, 2H), 5.27 (m, 1H), 7.28–7.45 (m, 6H), 9.41 (m, 1H), 9.68 (m, 1H).

TFA.Arg(Z)-Lactam (6)

Boc-Arg(Z)-Lactam (5) (38.0 g, 0.097 mole) was added to an R.B. flask containing a mixture of trifluoroacetic acid (200 ml) and anisole (20 ml). The trifluoroacetic acid (200 ml) and anisole 20 ml). The reaction mixture was stirred at 0° C. for 1 hr. The reaction was then concentrated in vacuo without heating. Diethylether (400 ml) was added, and the resulting solid was filtered, washed with diethylether, then dried in vacuo to give 40.5 g of the title compound (103% of theory): TLC R$_f$ (C) 0.29; FD-MS 291 (MH$^+$).

Boc-D-1-Tiq-Pro-Arg(Z)-Lactam (7)

In flask 1, Boc-D-1-Tiq-Pro-OH (3) (17.8 g, 47.5 mmole) was dissolved in DMF (100 ml) and cooled to −15° C. N-methylmorpholine (5.3 ml, 52.3 mmole) was then added, followed by the addition of isobutylchloroformate (6.2 ml, 47.5 mmole). The reaction mixture was stirred at −15° C. for 2 min.

In flask 2, TFA.Arg(Z)-Lactam (6) (19.2 g, 47.5 mmole) was dissolved in DMF (40 ml) and cooled to 0° C. N-methylmorpholine (5.3 ml, 52.3 mmole) was then added to the solution. The reaction mixture was stirred at 0° C. for 2 min.

The contents of flask 2 was added to flask 1, and the reaction mixture was stirred for 4 hr at −15° C. The reaction mixture was slowly warmed to R.T. overnight, followed by the addition of 5% NaHCO$_3$ (5 ml). The reaction solvent was removed in vacuo and a solution of EtOAc (175 ml) in water (150 ml) was added to the oil. The organic layer was separated then sequentially washed with 5% NaHCO$_3$, water, 0.1N HCl, and again with water. The organic solution was dried over magnesium sulfate and concentrated to dryness in vacuo yielding an amorphous solid (24.3 g) of the title compound (79% of theory): TLC R$_f$ (A) 0.71; FAB-MS 647 (MH$^+$); [a]$_D$=−32.8° C=0.5 CHCl$_3$ Boc-D-1-Tiq-Pro-Arg(Z)-H (8)

Boc-D-1-Tiq-Pro-Arg(Z)-Lactam (7) (23.4 g, 36.2 mmole) was dissolved in dry THF (300 ml) and placed in an R.B. flask under a nitrogen atmosphere. The reaction was then cooled to −70° C. Lithium aluminium hydride 1M in THF (37 ml, 37 mmole) was added dropwise to the reaction over 30 min. The reaction was then stirred at −70° C. for 30 min. A solution of THF (20 ml) and 0.5N H$_2$SO$_4$ (20 ml) was added dropwise to the reaction mixture over 10 min. The reaction was then diluted with a solution of EtOAc (400 ml) in water (400 ml). The EtOAc layer was separated, then washed 2 times with water (150ml). The organic solution was dried over magnesium sulfate, concentrated to dryness in vacuo resulting in 21 g of an amorphous solid of the title compound (89% of theory): TLC R$_f$ (A) 0.28.

D-1-Tiq-Pro-Arg-H Sulfate (9)

Boc-D-1-Tiq-Pro-Arg(Z)-H (8) (18.1 g.27.9 mmole) was dissolved in a solution of THF (200 ml) and water (80 ml). 1N H$_2$SO$_4$ (28 ml) and 5% Pd/C (3.0 g) was then added to the reaction. The reaction was subjected to hydrogenation under ambient temperature and pressure for 5 hr. the reaction was flushed with nitrogen and the catalyst was then removed by filtration through a hyflo pad. The filtrate was concentrated to 100 ml in vacuo followed by the addition of n-BuOH (200 ml) to the concentrate. The organic layer was separated, and the aqueous layer was extracted 3 times with n-BuOH (100 ml). The extracted organic layers were then combined and concentrated in vacuo. The residue was triturated with Et$_2$O/diisopropyl ether (1:1), and the solid was filtered and dried in vacuo yielding 11.08 g of crude material.

The solid (10.8 g, 19.2 mmole) was dissolved in a solution of water (20 ml) and 10N $H_2SO_4$ (20 ml). The reaction was heated to 50° C. and held for 25 min. The reaction was cooled to room temperature and the pH of the solution was adjusted to 4.0 with BioRad AG1-X8 resin (hydroxide form). The resin was then filtered, and the solution was lyophilized, yielding 8.44 g of crude title compound.

A sample of the crude title compound (4.2 g) was then dissolved in 0.01% $H_2SO_4$ and applied to two, in series, 5×25 cm, Vydac $C_{18}$ resin columns. A 2% to 10% linear gradient of of $CH_3CN$ was used to elute the peptide from the column. Column fractions were collected and pooled based on analytical RP-HPLC profiles. The combined fractions were adjusted to pH 4.0 using AG1-X8 resin (Bio-Rad analytical anion exchange resin 50–100 mesh) in hydroxide form. The resulting solution was filtered, and the filtrate was lyophilized to dryness yielding 2.4 g of purified peptide (57% of theory). FAB-MS 415($MH^+$); Amino acid analysis: Pro, 0.92; Tiq, 1.00; $[a]_D$=−76.12° C=0.5/0.01N $H_2SO_4$; EA: (calcd) $C_{21}H_{32}N_6O_7S$ C, 49.21; H, 6.29; N, 16.29; S, 6.26. Found: C, 51.20; H, 6.17; N, 16.88; S, 5.37.

EXAMPLE 2

Synthesis of D-3-Piq-L-Pro-L-Arg-H
D-1,2,3,4-Tetrahydro-3-isoquinolinecarboxylic acid (1)

D-phenylalanine (50 g, 302 mmol) was reacted with a 37% solution of formaldehyde (120 mL) and concentrated HCl (380 mL) at reflux temperature. After refluxing for 30 min, an additional 50 mL of formaldehyde was added, and the reaction was refluxed for an additional 3 hr. The reaction was cooled to −10° C., and the precipitate was removed by filtation. The solid was dried in vacuo to give pure title compound (24.2 g, 45%) FD-MS 178 ($MH^+$).

D-1,2,3,4,6,7,8-Perhydro-3-isoquinolinecarboxylic acid (2)

A solution of D-1,2,3,4-tetrahydro-3-isoquinolinecarboxylic acid (1) (17 g, 96 mmol) in water (200 mL) and 20 ml of 5N HCl was reacted with 5% $Rh/Al_2O_3$ (8.5 g) at 2000 psi in a high pressure apparatus at 120° C. for 16 hr. The reaction mixture was filtered through a Celite pad, and the filtrate was freeze dried to give pure title compound (21 g, 100%) FD-MS 184 ($MH^+$).

Cbz-D-1,2,3,4,6,7,8-Perhydro-3-isoquinolinecarboxylic acid (3)

D-3-Piq-OH (2) (21.0 g, 95.8 mmol) was dissolved in tetrahydrofuran (75 mL) and water (50 mL). The pH of the solution was adjusted to 10.0 with 5N NaOH. Benzyl chloroformate (16.4 mL, 115 mmol) was added dropwise, and the pH was maintained at 9.5 with 2N NaOH. The reaction mixture was stirred for an additional 1 hr at room temperature. The organic solvent was evaporated in vacuo, and the resulting residue was disolved in diethylether (100 mL) and water (50 mL). The aqueous layer was extracted, and adjusted to pH 3.0 with 3N HCl. Ethyl acetate (250 mL) was then added to the aqueous solution, and the organic layer was separated and dried over magnesium sulfate. The filtrate was concentrated in vacuo to give a clear oil of pure title compound (25.3 g, 85%) FD-MS 318 ($MH^+$); $[a]_D$=−5.1° C=0.5 MeOH Cbz-D-1,2,3,4,6,7,3-Perhydro-3-isoquinolinecarboxyl-L-Prolyl-t-butylester (4)

Cbz-D-3-Piq-OH (3) (17.2 g, 54 mmol) was dissolved in DMF (50 mL) and cooled to 0° C. Proline-t-butylester (9.2 g, 54 mmol), 1-hydroxybenzotriazole (7.3 g, 54 mmol), and DCC (11.1 g, 54 mmol) was then added to the solution. The reaction was stirred for 3 hr at 0° C., followed by 24 hr of stirring at room temperature. The reaction precipitate was filtered, and the filtrate concentrated in vacuo to an oil. The oil was then dissolved in EtOAc (200 mL) and water (100 mL). The organic layer was separated and sequentially washed with 1N $NaHCO_3$, water, 1.5N citric acid, and again water. The organic layer was dried over magnesium sulfate, and the filtrate was evaporated to an oil which then was dried to give the title compound (23.8 g, 94%) FAB-MS 471 ($MH^+$); TLC $R_f$ (A) 0.73; $[a]_D$=−40.0° C=0.5 MeOH Cbz-D-1,2,3,4,6,7,8-Perhydro-3-isoquinolinecarboxyl-L-Proline (5)

Cbz-D-3-Piq-Pro-O-t-Bu (4) (31.2 g, 66.3 mmole) was placed in an R.B. flask containing trifluoroacetic acid (100 ml), anisole (5 ml), and stirred at room temperature for 1 hr. The reaction was concentrated in vacuo without heating followed by the addition of diethylether (150 ml) and water (100 mL). The pH of the solution was adjusted to 9.8 with 5N NaOH. The aqueous layer was separated and adjusted to pH 2.8 with 3N HCl. Ethylthyl acetate (200 mL) then was added to the aqueous solution and the organic layer was separated, dried over magnesium sulfate, and the filtrate was concentrated in vacuo to give a clear oil. The oil was dissolved in diethylether (300 mL), and the solution was allowed to stand at room temperature for 24 hr. The resulting solid was filtered, washed with diethylether, and dried to give the title compound (13.5 g, 49%) FAB-MS 415 ($MH^+$); $[a]_D$=−57° C=0.5 MeOH; elemental analysis (calcd) $C_{23}H_{30}N_2O_5$: C, 66.65; H, 7.29; N, 6.76. Found: C, 66.90, H, 7.33, N, 6.81.

EXAMPLE 3

Synthesis of D-3-Tiq-L-Pro-L-Arg-aldehyde
D-1,2,3,4-Tetrahydro-3-isoquinolinecarboxylic acid (1)

D-phenylalanine (50 g, 302 mmol) was reacted with a 37% solution of formaldehyde (120 mL) and concentrated HCl (380 mL) at reflux temperature. After refluxing for 30 min, an additional 50 mL of formaldehyde was added, and the reaction was refluxed for 3 hr. The reaction was cooled to −10° C., and the precipitate was filtered. The solid was dried in vacuo to give pure title compound (24.2 g, 45%) FD-MS 178 ($MH^+$); elemental analysis (calcd) $C_{10}H_{11}NO_2$: C, 67.78; H, 6.26; N, 7.90. Found: C, 68.05, H, 6.42, N, 7.88.

Cbz-D-1,2,3,4-Tetrahydro-3-isoquinolinecarboxylic acid (2)

D-3-Tiq-OH (1) (40.0 g, 225 mmol) was dissolved in tetrahydrofuran (200 mL) and water (200 mL). The pH of the solution was adjusted to 9.5 with 5N NaOH. Benzyl chloroformate (35.4 mL, 248 mmol) was added dropwise while maintaining the pH at 9.5 with 2N NaOH. The reaction was stirred for an additional 1 hr at room temperature. The organic solvent was evaporated in vacuo, followed by the addition of diethylether (200mL) and water (50 mL). The aqueous layer was separated, and the pH of the solution was adjusted to 2.8 with 5N HCl. Ethyl acetate (250 mL) was added to the solution, and the organic layer was separated and dried over magnesium sulfate. The filtrate was concentrated in vacuo to give a clear oil of pure title compound (70.0 g, 100%) FD-MS 312 ($MH^+$).

Cbz-D-1,2,3,4-Tetrahydro-3-isoquinolinecarboxyl-L-Prolyl-t-butylester (3)

Cbz-D-3-Tiq-OH (3) (70.0 g, 225 mmol) was dissolved in DMF (150 mL) and cooled to 0° C. Proline-t-butylester (38.5 g, 225 mmol), 1-hydroxybenzotriazole (30.4 g, 225 mmol), and DCC (46.4 g, 225 mmol) were added to the reaction mixture. The reaction was stirred for 3 hr at 0° C. then stirred for an addition 24 hr at room temperature. The reaction precipitate was filtered, and the filtrate was concentrated in vacuo to an oil. The oil was dissolved in EtOAc (250 mL), water (125 mL), and the organic layer was separated and washed with 1N NaHCO$_3$, water, 1.5N citric acid, and again water. The organic layer was dried over magnesium sulfate, and the filtrate was evaporated to an oil which was dried to give the title compound (93.8 g, 89%) FAB-MS 464 (M$^+$); TLC R$_f$ (A) 0.76; [a]$_D$=−30.4° C=0.5 MeOH Cbz-D-1,2,3,4-Tetrahydro-3-isoquinolinecarboxyl-L-Proline (4)

Cbz-D-3-Tiq-Pro-O-t-Bu (3) (93.6 g, 200 mmole) was placed in an R.B. flask containing trifluoroacetic acid (150 ml) and anisole (7.5 ml) and stirred at room temperature for 1 hr. The reaction was concentrated in vacuo without heating. Diethylether (150 ml) and water (200 mL) was added, and the pH of the solution was adjusted to 9.8 with 5N NaOH. The aqueous layer was separated, adjusted to pH 2.5 with 5N HCl followed by the addition of ethyl acetate (250 mL). The organic layer was separated, dried over magnesium sulfate, and the filtrate was concentrated in vacuo to give a clear oil. The oil was dissolved in diethylether (300 mL), and dicyclohexylamine (40 mL, 200 mmole) then was added to the solution. The resulting solution was allowed to stand at room temperature for 24 hr. The solid was filtered washed with diethylether and dried to give the DCHA salt of the title compound (103.7 g, 88%) FAB-MS 409 (MH$^+$); [a]$_D$=−24.5° C=0.5 MeOH.

Final synthesis was completed in substantial accordance with the coupling reactions described in Example 1 to give D-1-Tiq-L-Pro-L-Arg-aldehyde. FAB-MS 415 (MH$^+$); [a]$_D^a$=−13°; elemental analysis (calcd) $C_{21}H_{30}N_6O_3 \cdot H_2SO_4 \cdot 2H_2O$: C, 46.03; H, 6.62; N, 15.33. Found: C, 46.33, H, 6.04, N, 15.04.

EXAMPLE 4

Synthesis of D-3-Tiq(7-OH)Pro-Arg-H. 2HCl

H-D-3-Tiq(7-OH)-OH was purchased from Peptides International (Catalog # ADX-5026-PI; Louisville, Ky.) and was used as the starting material to prepare the title compound in substantial accordance with the steps in Example 3. FAB-MS 431 (MH$^+$); [a]$_D^a$=−1.2°; elemental analysis (calcd) $C_{21}H_{30}N_6O_4 \cdot 2HCl \cdot H_2O$: C, 48.37; H, 6.52; N, 16.12. Found C, 48.28; H, 6.14; N, 15.53.

EXAMPLE 5

In Vivo Assay

Adult male beagle dogs weighing approximately 9–14 kg were anesthetized with pentobarbital sodium (30 mg/kg, i.v.). The tracheae were intubated, and the dogs were ventilated with room air delivered from a Harvard respirator (ventilation rate of 16 cycles/min, tidal volume, 25 ml/kg). Body temperature was maintained at 37–°38° C. with a heating pad. Catheters were placed in the left femoral artery and vein for measurement of phasic arterial blood pressure (Starham transducer, P23ID) and i.v. infusion of drug solutions, respectively. Mean arterial blood pressure was calculated as diastolic blood pressure plus ⅓ pulse pressure. Cardiac rate was monitored by a cardiotachometer that was triggered by the systolic pressure pulse, while the pressure rate product was monitored as an index of myocardial oxygen demand. See Gobel et al.: The rate pressure product as an index of myocardial oxygen consumption during exercise in patients with angina pectoris; *Circulation* 57: 549–556, (1978). Subdermal electrodes were used to record a Lead II electrocardiogram for assessing ST-segment alteration and estimating the incidence and duration of arrhythmia. Directly measured parameters were recorded continuously on a multichannel oscillograph (Beckman Instruments, Inc., Fullerton Calif.; model R611).

A left thoracotomy was performed at the fifth intercostal space, the heart was suspended in a pericardial cradle, and the left circumflex coronary artery (LCX) was isolated distal to its atrial branch and proximal to any major ventricular branches. Baseline circumflex coronary artery blood flow was measured using a calibrated flowprobe (Carolina Medical Electronics, 6 mm I.C.) connected to a Carolina flowmeter (model FM501). Initially, each dog was fitted with a critical coronary stenosis by tying a ligature around the LCX and an interposed 18–19 gauge needle, and then removing the needle to allow blood flow through a diameter the size of the needle. The critical stenosis was adjusted to attenuate by more than 70% the peak blood flow increment produced by a 10 sec complete occlusion of the LCX, without altering baseline blood flow. Use of the critical stenosis in this manner has been reported (Sheehan, F. and Epstein, S.: Determinants of arrhythmic death due to coronary artery spasm: Effect of preexisting coronary artery stenosis on the incidence of reperfusion arrhythmia. *Circ. Res.* 65: 259–264, 1982) to limit reperfusion hyperemia and associated cardiac arrhythmias, and the potential for ventricular fibrillation. The coronary flowprobe was removed following placement of the critical stenosis.

After placement of the critical stenosis and an equilibration period, baseline parameters were recorded and the LCX was completely occluded using a snare. Total occlusion of the LCX was maintained for 1 hr and was followed by 5 hr of reperfusion after removal of the snare. The critical stenosis was kept in place through the initial 30 min of reperfusion. ST-segment deviation was measured periodically during the hr of LCX occlusion, while the intensity and duration of cardiac arrhythmia was assessed hourly using a semi-quantitative rating scale: 1=minimal, 2=moderate, 3=severe. Experiments were conducted using either a pretreatment or reperfusion drug treatment protocol. In the pretreatment protocol, an i.v. infusion of saline or drug solution was begun 15 min prior to LCX occlusion and continued until the end of the 5 hr reperfusion period. In the reperfusion protocol, a continuous 5 hr i.v. infusion of saline or drug solution was begun at the time of reperfusion, following 1 hr of LCX occlusion.

Following reperfusion, the heart was rapidly excised for infarct measurement using the triphenyltetrazolium/Evans blue dual-dye staining procedure of Shea (Shea et al.: The beneficial effects of nafazatrom (Bay g 6575) on experimental coronary thrombosis; *Am. Heart J.* 107: 629–637, 1984; and Shea et al.: Beneficial effects of nafazatrom on ischemic reperfused myocardium. *Eur. J. Pharmacol.* 102: 63–70, 1984), as modified by Hahn (Hahn et al.: Antagonism of leukotriene B$_4$ receptors does not limit canine myocardial infarct size. *J. Pharmacol. Exp. Ther.* 253: 58–66, 1990). Cannulae were inserted into the aorta above the coronary ostia and into the LCX at the site of previous occlusion. The LCX bed was perfused with a 1.5% solution of triphenyltetrazolium in 20 mM potassium phosphate buffer (pH 7.4, 38° C.), while the remainder of the heart was perfused simultaneously, via the aorta, with 0.1% Evans blue in saline. Perfusion pressure was maintained constant at 100 mm Hg and the duration of myocardial perfusion was approximately 5 min. The heart was then sectioned perpendicular to the apex-base axis into six slabs of approximately 1 cm thickness. Myocardium perfused by coronary arteries other than the circumflex was stained blue, viable left ventricle within the distribution of the circumflex artery (mass at risk) was stained brick-red, whereas infarcted left ventricle within the mass at risk was unstained. Each transverse section was trimmed of right ventricular muscle and valvular and fatty tissue, blotted dry and then traced onto a clear plastic overlay for planimetric measurement of the size of the respective areas. Each area of myocardium also was dissected and weighed for gravimetric quantitation. Sectional and cumulative infarct size were expressed as a percentage of the mass of left ventricle placed at risk.

TABLE 1

Influence of Test Compounds on Myocardial Infarct Size Following Coronary Artery Occlusion and Reperfusion

| Treatment | Protocol | Infusion Rate (mg/kg/hr) | Infarct Size[a] |
|---|---|---|---|
| Saline | — | — | 42.4 ± 4.0[b] |
| Compound 6 | Pretreatment | 2.0 | 25.1 ± 5.9[c] |
| Saline | — | — | 40.1 ± 4.1 |
| Compound 6 | Reperfusion | 2.0 | 26.5 ± 4.7[c] |
| Saline | — | — | 38.4 ± 3.4 |
| Compound 5 | Reperfusion | 0.5 | 24.1 ± 6.3[c] |
| Saline | — | — | 48.3 ± 5.8 |
| Compound 5 | Reperfusion | 1.0 | 28.9 ± 3.5[c] |
| Saline | — | — | 38.4 ± 3.4 |
| Compound 3 | Reperfusion | 1.0 | 19.0 ± 2.6[c] |
| Saline | — | — | 48.3 ± 5.8 |
| Compound 4 | Reperfusion | 1.0 | 26.0 ± 5.5[c] |
| Saline | — | — | 44.0 ± 4.4[b] |
| Compound 1 | Reperfusion | 1.0 | 17.5 ± 2.7[c] |
| Saline | — | — | 45.9 ± 6.6 |
| Compound 2 | Reperfusion | 1.0 | 21.8 ± 4.3[c] |

[a]Infarct size units = % Infarct Mass/Mass at risk.
[b]Mean value of 8–9 dogs.
[c]Statistically significant from saline control (P < 0.05).

The data in Table 1 illustrated that the tested experimental compounds each was able to contain myocardial infarct size resulting from coronary artery occlusion and reperfusion when administered in a clinically relevant protocol. Because coronary artery occlusion and reperfusion were produced by a mechanical snare, infarct containment efficacy was not due to prevention of a large occlusive thrombus within the infarct-related artery. The salvage of ventricular tissue by each of these compounds occurred with little or no overt cardiovascular, electrocardiographic and bleeding liabilities.

The precise mechanism by which the compounds of formula 1 limited ischemic injury is not known. This biological activity may be associated with the protease inhibition properties of the compounds. Aprotinin, a serine protease inhibitor know to antagonize at least plasmin, trypsin, and kallikrein, has been shown to limit myocardial ischemic injury associated with coronary artery occlusion (Diaz et al.; Effect of Kallikrein Inhibitor Aprotinin on Myocardial Ischemic Injury Following Coronary Artery Occlusion in the Dog, Am. J. Cardiol. 40: 541–549, 1977). We also have demonstrated aprotinin to significantly reduce myocardial infarct size that occurs in response to coronary artery occlusion and reperfusion; infarct size was 37.9±5.4% of the left ventricular mass at risk of necrosis in control dogs and 24.8±2.4% (P<0.05) in dogs infused with aprotinin. Whether the mechanisms by which aprotinin or the compounds of formula 1 are similar, or are identical is not known.

The above studies also included an evaluation of leukocyte (neutrophil) disposition in a setting of evolving myocardial infarction. None of the tested compounds of formula 1 significantly altered the development of systemic leukocytosis in response to ischemic injury, or the accumulation of leukocytes within ischemic and infarcted myocardium.

In summary, a representative sample of compounds of formula 1 all demonstrated the ability to minimize and contain tissue damage brought on by ischemia and reperfusion. This important therapeutic property was established by showing that all the tested compounds contained myocardial infarction resulting from coronary artery occlusion and roperfusion. As such the compounds of formula 1 are useful in a novel method for minimizing and containing reperfusion damage to tissues. Most significantly, the compounds of formula 1 are particularly useful in the treatment of myocardial infarction in humans.

We claim:

1. A method of treatment for minimizing and containing reperfusion injury in mammals which comprises administering to a mammal in need of such treatment an effective non-toxic amount of a compound of the general formula:

A-Pro-Arg-H wherein substituent A has an α-carbon, the stereochemical configuration of which is either D or L, preferably D, and wherein Pro and Arg are both of the L configuration;

A is

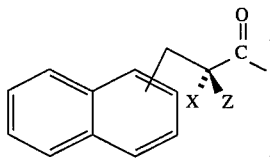

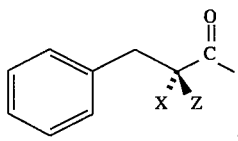

1 or 2

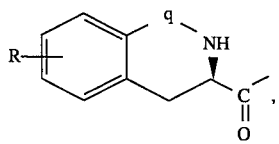

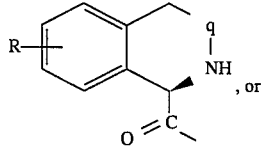
, or

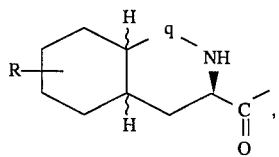

Z is $C_1$–$C_4$ alkyl, or H;

X is $NH_2$, NHZ, t-butyloxycarbonyl-NH, acetyl-NH, or trifluoroacetyl-NH;

R is H, OH, halogen, alkoxy, $CF_3$, $C_1$–$C_4$ alkyl, $NO_2$, or $NH_2$; and, q is $CH_2$, or CO.

2. The method of claim 1 wherein the administering is done by intravenous infusion.

3. The method of claim 2 wherein the mammal in need of treatment is a mammal experiencing evolving myocardial infarction.

4. The method of claim 3 wherein the mammal is a human being.

5. The method of claim 1 wherein the compound is co-administered with an effective, non-toxic amount of aspirin.

6. The method of claim 2 wherein the compound is co-administered with an effective, non-toxic amount of aspirin.

7. The method of claim 3 wherein the compound is co-administered with an effective, non-toxic amount of aspirin.

8. The method of claim 4 wherein the compound is co-administered with an effective, non-toxic amount of aspirin.

9. A method for minimizing and containing reperfusion injury in mammals which comprises administering to a mammal in need of such treatment an effective non-toxic amount of a compound selected from the group consisting of D-3-Piq-L-Prolyl-L-Arginal, D-7-hydroxyl-1,2,3,4-Tiq-3-carbonyloxy-L-Prolyl-L-Arginal, D-3-Tiq-L-Prolyl-L-Arginal, D-1,2,3,4-Tiq-1-carbonyl-L-Prolyl-L-Arginal, N-Methyl-D-Phenylalanyl-L-Prolyl-L-Arginal, and $N^{\alpha}$-t-butyloxycarbonyl-D-Phenylanyl-L-Prolyl-L-Arginal.

10. The method of claim 9 wherein the administering is done by intravenous infusion.

11. The method of claim 10 wherein the mammal in need of treatment is a mammal experiencing evolving myocardial infarction.

12. The method of claim 11 wherein the mammal is a human being.

13. The method of claim 9 wherein the compound is co-administered with an effective, non-toxic amount of aspirin.

14. The method of claim 10 wherein the compound is co-administered with an effective, non-toxic amount of aspirin.

15. The method of claim 11 wherein the compound is co-administered with an effective, non-toxic amount of aspirin.

16. The method of claim 12 wherein the compound is co-administered with an effective, non-toxic amount of aspirin.

17. The method of claim 1 wherein the administered compound is D-3-Piq-L-Prolyl-L-Arginal.

18. The method of claim 1 wherein the administered compound is D-7-hydroxyl-1,2,3,4-Tiq-3-carbonyloxy-L-Prolyl-L-Arginal.

19. The method of claim 1 wherein the administered compound is D-3-Tiq-L-Prolyl-L-Arginal.

20. The method of claim 1 wherein the administered compound is D-1,2,3,4-Tiq-1-carbonyl-L-Prolyl-L-Arginal.

21. The method of claim 1 wherein the administered compound is N-Methyl-D-Phenytalanyl-L-Prolyl-L-Arginal.

22. The method of claim 1 wherein the administered compound is $N^{\alpha}$-t-butyloxycarbonyl-D-Phenylanyl-L-Prolyl-L-Arginal.

* * * * *